United States Patent
Palla et al.

(10) Patent No.: US 6,228,885 B1
(45) Date of Patent: May 8, 2001

(54) FUNGICIDAL COMPOSITIONS BASED ON (N-PHENYLACETYL-N-2,6-XYLYL)METHYL ALANINATE

(75) Inventors: Ottorino Palla, Crema; Luigi Mirenna, Milan; Laura Colombo, Lodi; Guido Zini, Novars; Lucio Filippini, Milan; Giampaolo Zanardi, Novara, all of (IT)

(73) Assignee: Isagro S.p.A., Milan (IT)

( * ) Notice: Subject to any disclaimer, the term of this patent is extended or adjusted under 35 U.S.C. 154(b) by 0 days.

(21) Appl. No.: 09/331,168
(22) PCT Filed: Dec. 6, 1997
(86) PCT No.: PCT/EP97/06968
§ 371 Date: Sep. 27, 1999
§ 102(e) Date: Sep. 27, 1999
(87) PCT Pub. No.: WO98/26654
PCT Pub. Date: Jun. 25, 1998

(30) Foreign Application Priority Data

Dec. 19, 1996 (IT) ............................... MI96A2660
May 22, 1997 (IT) ............................... MI97A1198

(51) Int. Cl.$^7$ .................................................. A01N 37/12
(52) U.S. Cl. ........................... 514/538; 504/142; 504/149
(58) Field of Search ................................ 562/43; 514/538; 504/149, 142

(56) References Cited

FOREIGN PATENT DOCUMENTS

WO 96/01559   1/1996   (WO) .
WO 96/01560   1/1996   (WO) .

OTHER PUBLICATIONS

F. Gozzo, et al., Pesticide Science, vol. 16, pp. 277–286, "Recent Progress in the Field of N–acylalanines as Systemic Fungicides," 1985.

*Primary Examiner*—Paul J. Killos
(74) *Attorney, Agent, or Firm*—Oblon, Spivak, McClelland, Maier & Neustadt, P.C.

(57) ABSTRACT

When used in admixture with mancozeb, chlorothalonil, a copper salt, folpet, fluazinam or cymoxanil (this being possible for the latter to be used also together with one of the other five components), metalaxyl having a high R-enantiomer content of more than 70% by weight, or pure R-metalaxyl, exhibits a markedly increased fungicidal action against plant diseases as compared with a similar mixture in which metalaxyl is used in the form of the racemate.

32 Claims, No Drawings

FUNGICIDAL COMPOSITIONS BASED ON (N-PHENYLACETYL-N-2,6-XYLYL)METHYL ALANINATE

BACKGROUND OF THE INVENTION

1. Field of the Invention

The present invention relates to fungicidal compositions based on (N-phenylacetyl-N-2,6-xylyl)methyl alaninate.

2. Description of the Background

More specifically, the present invention relates to fungicidal compositions comprising the compound corresponding to (N-phenylacetyl-N-2,6xylyl)methyl alaninate, in which more than 50% of said compound consists of the laevorotatory enantiomorph, and one or more known fungicides and their use in the agricultural field for controlling fungine disease which seriously damage agricultural crops.

Many of the compounds which are used for controlling phytopathogen fungi in agrarian practice have at least one asymmetrical centre. In particular, when these compounds have only one asymmetrical centre, or chiral centre, the two enantiomorphs can have a different fungicidal activity.

More specifically, when only one of the enantiomorphs has a significant biological activity, it is possible for the same fungicidal effect to be obtained using the more efficient enantiomorph at a dosage which is half that of the raceme. Obviously when both enantiomorphs have a comparable biological activity, the reductions in the expected applicative dosages should in any case be less than 50% with respect to those of the raceme.

Most fungicidal compounds containing at least one chiral centre are normally sold as a racemic mixture as it is difficult to compensate the higher cost relating to the production of the enantiomorph in its pure form, with additional commercial advantages.

The necessity of improving the environmental impact has recently led to a re-evaluation of the use of single enantiomorphs to obtain at least partial reductions in the dosages used, thus diminishing the quantity of xenogene substances dispersed in the environment and improving the environmental impact of phytoiatric treatment.

In addition, it is particularly advantageous if products with a fungicidal activity can be easily degraded by the vegetable host at the end of the period for which the fungicidal activity is required, so as to guarantee the minimum quantity of residual active principle.

The reduction in residues of main principle in vegetables when they are picked, is in fact linked to potential risk for possible consumers of the agricultural product: the smaller the quantity of residual active principle, the lower the risk will be for the consumer.

The compound (N-phenylacetyl-N-2,6-xylyl)-DL-methyl alaninate, also known under the trade-name of Benalaxyl, is particularly efficient in the control of diseases caused by Oomycetes. Oomycetes are responsible for many diseases of economically important crops such as, for example, grapes, potatoes, tomatoes and tabacco. This fungicide is described in U.S. Pat. Nos. 4,291,049 and 4,425,357.

Benalaxyl has one asymmetrical centre and consists of an equimolecular mixture of the two enantiomorphs. When prepared according to the methods described in the two U.S. patents cited above, Benalaxyl is obtained as a racemic mixture in which the enantiomorphs are present in equimolecular quantities.

"Pesticide Science" (1985), Vol. 16, pages 277–286, on the other hand also describes the preparation of the laevorotatory enantiomorph, corresponding to (N-phenylacetyl-N-2,6-xylyl)-D-methyl alaninate and shows its greater activity with respect to both the dextrorotatory enantiomorph corresponding to (N-phenylacetyl-N-2,6-xylyl)-L-methyl alaninate and the raceme, correspondingto (N-phenylacetyl-N-2, 6-xylyl)-DL-methyl alaninate. This greater activity has been observed by both experimenting the laevorotatory enantiomorph in tests in vitro, and by applying it on infected plants or on plants infested after its application, and also by applying it to the earth or plant seed, to control the pathogenes present in the soil.

Racemic Benalaxyl is degraded with a different rate depending on the type of vegetable and portion to which it is applied.

For example, the degradation rate of racemic Benalaxyl in hops makes the use of this product unsuitable as an antifungal agent, to the detriment of its distinct fungicidal efficiency: in fact, after two weeks following treatment, the residual levels of active principle are still high.

Together with its good preventive activity, Benalaxyl also has considerable curative efficiency: it is in fact capable of blocking infections already in development consequently allowing intervention after infection. In agrarian practice it is customary to intervene within 72 hours of a possible infection such as, for example, rainfall or abundant nightdew.

Literature of the known art specifies that the MIC (minimum concentration of active principle necessary for inhibiting the development of disease) of the laevorotatory enantiomorph of Benalaxyl, when applied on the leaves of vines cultivated in a vase and infected 24 hours earlier with spores of *Plasmopara viticola*, is 5 mg/l, the MIC of the dextrorotatory enantiomorph is 100 mg/l and the MIC of the raceme is 10 mg/l.

SUMMARY OF THE INVENTION

The Applicants have now surprisingly found that the laevorotatory enantiomorph of Benalaxyl, corresponding to (N-phenylacetyl-N-2,6-xylyl)-D-methyl alaninate applied to leaves combined with one or more fungicides normally used for controlling phytopathogenic Oomycetes of economically important crops, has a higher synergetic activity than that possbily obtained with the racemic product used in a double dosage, consequently containing the same quantity of laevorotatory enantiomorph. This allows the production of more effective fungicidal compositions, having an improved environmental impact with respect to those obtained using racemic Benalaxyl.

DETAILED DESCRIPTION OF THE PREFERRED EMBODIMENTS

The present fungicidal compositions can be used in both curative and preventive applications, i.e. at regular intervals. In treatment at regular intervals, its curative property is still important to fight infections which have possibly arisen during the last period of the interval of treatment.

The present invention therefore relates to fungicidal compositions comprising:
(a) the compound corresponding to (N-phenylacetyl-N-2,6-xylyl)methyl alaninate having formula (I):

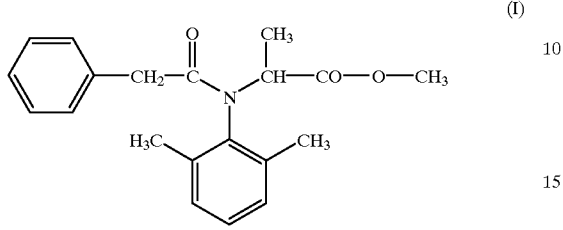

(I)

wherein more than 50% of said compound having formula (I) consists of the laevorotatory enantiomorph;
(b) one or more fungicides selected from:
(1) Cymoxanil corresponding to 1-(2-cyano-2-methoxyiminoacetyl)-3-ethyl-urea;
(2) Fosetyl having the formula:

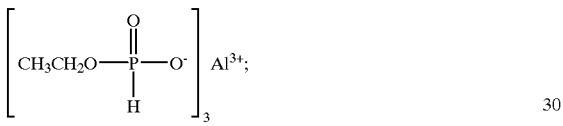

(3) Metalaxyl corresponding to methyl-N-(2-methoxyacetyl)-N-2,6-xylyl-DL-alaninate;
(4) Oxadixyl corresponding to 2-methoxy-N-(2-oxo-1,3-oxazolidin-3-yl)-acet-2'-6'-xylidine;
(5) Ofurace corresponding to DL-3-[N-chloroacetyl-N-(2,6-dimethylphenyl)-amino]-γ-butyrolactone;
(6) Fluazinam corresponding to 3-chloro-N-[3-chloro-2,6-dinitro-4-(trifluoromethyl)-phenyl]-5-trifluoromethyl-2-pyridinamine;
(7) (E)-2-[2-([6-(2-cyanophenoxy)-pyrimidin-4-yloxy]-phenyl-3-methyl methoxyacrylate;
(8) (E)-methoxyimino-α-o-tolyloxy)-o-tolyl]-methyl acetate;
(9) N-methyl-(E)-methoxyimino-[2-(2,5-dimethylphenoxymethyl)-phenyl] acetamide;
(10) N-methyl-(E)-methoxyimino-[2-phenoxyphenyl] a-cetamide;
(11) O-(1-methylethyl)-N-[2-methyl-1-[[[1-(4-chlorophenyl)-ethyl]-amino]-carbonyl]-propyl]-carbamate;
(12) O-(1-methylethyl)-N-[2-methyl-1-[[[1-(4-methylphenyl)-ethyl]-amino]-carbonyl]-propyl]-carbamate;
(13) O-(1-methylethyl)-N-[2-methyl-1-[[[1-(4-ethylphenyl)-ethyl]-amino]-carbonyl]-propyl]-carbamate;
(14) O-(1-methylethyl)-N-[2-methyl-1-[[[1-(4-methoxyphenyl)-ethyl]-amino]-carbonyl]-propyl]-carbamate;
(15) O-(phenyl)-N-[2-methyl-1-[[[1.(4-methoxyphenyl)-ethyl]-amino]-carbonyl]-propyl]-carbamate;

(16) compounds belonging to the group of dithiocarbamates having the general formula:

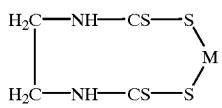

wherein M represents manganese or zinc;
(17) Thiram corresponding to bis-(dimethylthiocarbamoyl)-disulfide;
(18) Propineb having the formula:

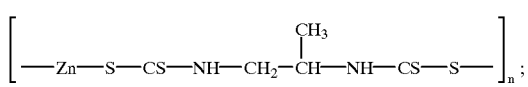

(19) Anilazine corresponding to N-(4,6-dichloro-1,3,5-triazin-2-yl)-aniline;
(20) Dichlofluanid having the formula:

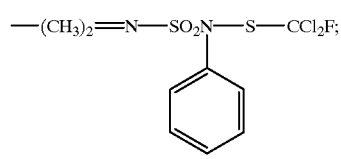

(21) Tolylfluanid having the formula:

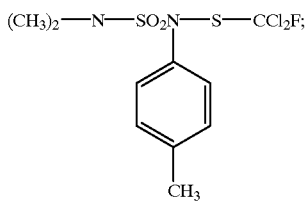

(22) Captan having the formula:

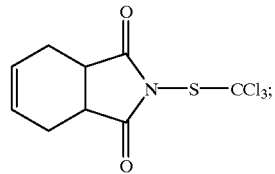

(23) Folpet having the formula:

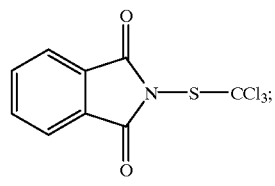

(24) Chlorothalonil corresponding to 1,3-di-cyano-2,4,5,6-tetrachlorobenzene;

(25) Dimethomorph having the formula:

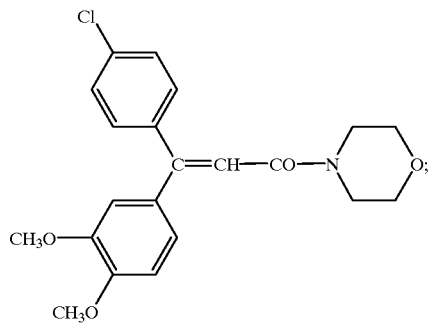

(26) Flumetover corresponding to N,N-diethylamide of 4-trifluoromethyl-6-(3,4-dimethoxyphenyl)-benzoic acid;

(27) Dithianon corresponding to 5,10-dihydro-5,10-dioxonaphthol-[2,3-b]-1,4-dithin-2,3-dicarbonitrile;

(28) Tetraconazole corresponding to 1-(1H-1,2,4-triazol-1-yl)-2-(2,4-dichlorophenyl)-3-(1,1,-2,2-tetrafluoroethoxy)-propane;

(29) Propiconazole corresponding to 1-[2-(2,4-dichlorophenyl)-4-propyl-1,3-dioxolan-2-yl-methyl]-1H-1,2,4-triazole;

(30) Triadimefon corresponding to 1-(4-chlorophenoxy)-3,3-dimethyl-1-(1H-1,2,4-triazol-1-yl)-butanone;

(31) Triadimenol corresponding to 1-(4-chlorophenoxy)-3,3-dimethyl-1-(1H-1,2,4-triazol-1-yl)-butan-2-ol;

(32) Bitertanol corresponding to 1-(diphenyl-4-yloxy)-3,3-dimethyl-1-(1H-1,2,4-trizaol-1-yl)-butan-2-ol;

(33) Etridiazole corresponding to ethyl 3-trichloromethyl-1,2,4-thiadiazolyl ether;

(34) Pencycuron corresponding to 1-(4-chlorobenzyl)-1-cyclopentyl-3-phenylurea;

(35) Hymexanol corresponding to 5-methylisoxazol-3-ol;

(36) Protiocarb corresponding to S-ethyl-(3-dimethylaminopropyl)-thiocarbamate;

(37) Propamocarb corresponding to propyl 3-(dimethylamino)-propylcarbamate;

(38) salts of copper (I) or copper (II);

(39) Andoprim corresponding to 2-p-methoxy-aniline-4,6-dimethyl-pyrimidine;

(40) Famoxadone or DPX-JE874 corresponding to 5-methyl-5-(4-phenoxyphenyl)-3-(phenylamino)-oxazolidin-2,4-dione;

(41) 4-methyl-4-phenyl-1-(phenylamino)-2-methylthio-imidazolidin-5-one;

(42) pyrimidinic compounds such as, for example, cyprodinil, mepanipyrim, pyrethanil;

(43) compounds having the following general formula:

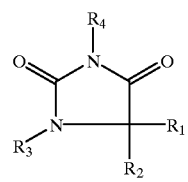

wherein:
$R_1$ and $R_2$, the same or different, represent a hydrogen atom; or a $C_1$–$C_3$ alkyl group; or, $R_1$ and $R_2$ together with the hydantoinic ring to which they are attached, represent a $C_3$–$C_7$ saturated spiro ring;
$R_3$ and $R_4$, different from each other, represent a $C_1$–$C_3$ alkyl group; a phenyl group, said phenyl group optionally substituted with a halogen atom, with a nitro group, with a $C_1$–$C_3$ alkoxyl group, or with a $C_1$–$C_3$ haloalkyl group; or a 3-iodo-propinyl group;

(44) compounds having the following general formula:

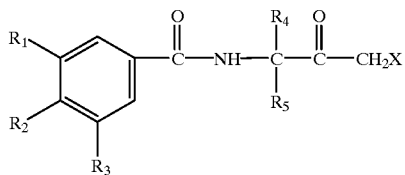

wherein:
$R_1$ and $R_3$, the same or different, represent a halogen atom; or a $C_1$–$C_4$ alkyl group;
$R_2$ represents a $C_1$–$C_4$ alkyl group; a $C_2$–$C_4$ alkenyl group; a $C_2$–$C_6$ alkinyl group; a $C_1$–$C_4$ alkoxyl group; a cyano group;
$R_4$ and $R_5$, the same or different, represent a halogen atom; or a $C_1$–$C_4$ alkyl group; on the condition that, at least one between $R_4$ and $R_5$, is a $C_2$–$C_4$ alkyl group;
X represents a halogen atom; a thiocyano group; an isothiocyano group;

(45) oligopeptidic compounds having the general formula:

wherein:
z and w, the same or different, are 1 or 2;
A represents an aminoacidic portion having the general formula:

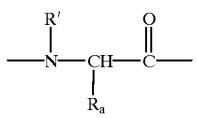

wherein:
$R_a$ represents a linear or branched $C_3$–$C_4$ alkyl group; or a $C_3$–$C_4$ cycloalkyl group;
R' represents a hydrogen atom; a $C_1$–$C_3$ alkyl group; or, together with $R_a$ it forms a linear or branched $C_3$–$C_5$ alkylene chain;

B represents an aminoacidic portion having the general formula:

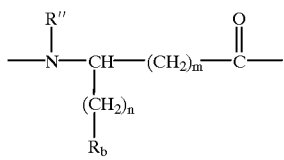

wherein:
  $R_b$ represents a phenyl group or an aromatic heterocyclic group, said phenyl and heterocyclic groups, also optionally substituted;
  m and n, the same or different, are 0 or 1;
  R" represents a hydrogen atom; or a $C_1-C_3$ alkyl group;
  L represents a group having the general formula:

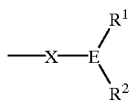

wherein:
  E represents a linear or branched $C_1-C_8$ alkylene chain; a linear or branched $C_2-C_8$ ω-oxalkyl chain; or a direct bond;
  $R^1$ represents a hydrogen atom; a $C_3-C_6$ cycloalkyl group; a phenyl group or an aromatic heterocyclic group, said phenyl and heterocyclic groups also optionally substituted;
  $R^2$ represents a hydrogen atom; a linear or branched $C_2-C_6$ carboxyalkyl group; a linear, branched or cyclic $C_2-C_6$ carbamoyl group; or a cyano group;
  X represents an —O— group; an —N($R^3$)— group; or an —N($R^4$)—O— group; wherein:
    $R^3$ represents a hydrogen atom; a $C_1-C_3$ alkyl or alkoxyl group; or, together with $R_1$, it represents a direct bond or a linear or branched $C_2-C_4$ alkylene chain;
    $R^4$ represents a hydrogen atom; a $C_1-C_3$ alkyl group; or, together with $R_1$, it represents a direct bond;
  K represents a hydrogen atom; a linear or branched $C_1-C_4$ alkyl group; or a protective group having general formula:

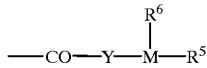

Y represents an oxygen atom; or a direct bond;
  M represents a linear, branched or cyclic $C_1-C_8$ alkylene chain; or a direct bond;
  $R^5$ represents a hydrogen atom; a phenyl group optionally substituted; a linear, branched or cyclic $C_2-C_6$ carbamoyl group; a linear, branched or cyclic $C_1-C_6$ carboalkoxyl group; or a cyano group;
  $R^6$ represents a hydrogen atom; a $C_1-C_3$ alkoxyl group; an acetate group; or an acetamidic group;
  (46) methylbenzothiadiazole-7-thiocarboxylate.

In the compositions of the present invention, the compound having general formula (I) preferably contains more than 90% of the laevorotatory enantiomorph, even more preferably at least 95% of the laevorotatory enantiomorph.

Compositions in which the compound having formula (I) contains at least 99% of the laevorotatory enantiomorph are even more preferred.

The laevorotatory enantiomorph corresponding to (N-phenylacetyl-N-2,6-xylyl)-D-methyl alaninate, has the following formula (II):

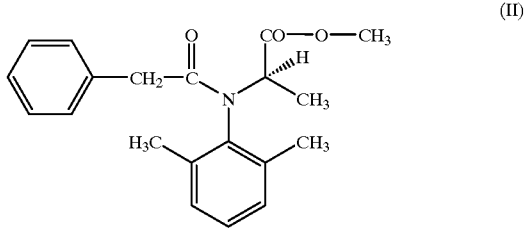

The asymmetrical carbon present in the compound having formula (II) has the absolute configuration defined in said formula (II); this configuration can be described as D-shaped, according to the actual terminology of aminoacids, or R-shaped according to the classification introduced by Cahn, Ingold and Prelog.

The improved environmental impact of the fungicidal compositions of the present invention is due to the fact that the compound having formula (I) in which more than 50% of said compound consists of the laevorotatory enantiomorph, has a lower residual level of active principle in crops treated when the fungicidal activity is completed (as already mentioned above, racemic Benalaxyl on the other hand has even higher residual levels of active principle after two weeks following treatment). The laevorotatory enantiomorph is therefore degraded more rapidly with respect to racemic Benalaxyl.

Tne compound having formula (I) can be conveniently prepared by various processes.

One process for the preparation of the compound having formula (I) comprises:

(a) reacting methyl ester having general formula (III):

having an S-type asymmetrical carbon and wherein X represents a halogen atom such as chlorine, fluorine, bromine or iodine; or X represents an activated ester such as a paratoluenesulfonate, a mesilate or triflate; with an xylidine having formula (IV):

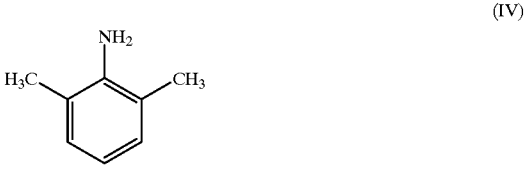

in the presence of or without an inert organic solvent or a mixture of inert organic solvents, at a temperature ranging from 60° C. to the boiling point of the solvent system selected, in the presence of or without an organic or inorganic base, obtaining N-xylyl-D-methyl alaninate having formula (V):

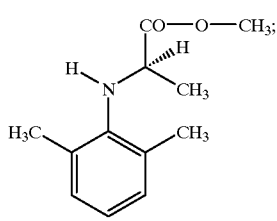

(V)

(b) acylating the N-xylyl-D-methyl alaninate having formula (V) obtained in step (a), with a derivative of phenylacetic acid such as, for example, acyl chloride; or with a mixed anhydride obtained by reaction of the salt of phenylacetic acid with an acyl chloride such as, for example, pivaloyl chloride; or with an alkyl chloroformate such as, for example, isobutyl chloroformate; in the presence of an inert organic solvent or a mixture of inert organic solvents, at a temperature ranging from −30° C. to +120° C., in the presence of or without an organic or inorganic base, obtaining the compound having formula (I).

Examples of inert organic solvents which can be used in step (a) of the above process are: aromatic solvents such as, for example, toluene, xylene; protic solvents such as, for example, ethanol, propanol, butanol, octanol; dipolar aprotic solvents such as, for example, N,N-dimethyl-formamide, N-methylpyrrolidone, dimethylsulfoxide; or their mixtures.

Examples of organic bases which can be used in step (a) of the above process are tertiary amines such as, for example, triethylamine.

Examples of inorganic bases which can be used in step (a) of the above process are alkaline carbonates or hydrogencarbonates such as, for example, sodium hydrogencarbonate and potassium carbonate.

The use of the above bases must, however, be carefully effected in order to avoid racemizations of the asymmetrical carbon.

Examples of inert organic solvents which can be used in step (b) of the above process are: esters such as, for example, ethyl acetate; chlorinated solvents such as, for example, methylene chloride, dichloroethane; aromatic solvents such as, for example, toluene, xylene; hydrocarbons such as, for example, hexane, petroleum ether; or their mixtures.

Examples of organic bases which can be used in step (b) of the above process are tertiary amines such as, for example, triethylamine, N-methylmorpholine; or heterocyclic amines such as, for example, pyridine.

Examples of inorganic bases which can be used in step (b) of the above process are alkaline carbonates such as, for example, sodium carbonate.

The Applicant has however surprisingly found, and this is therefore a further object of the present invention, that step (b) of the above process is conveniently carried out in the presence of an aromatic solvent (for example, toluene, etc.), or a halogenated solvent (for example, dichloromethane, dichloroethane, etc.) or an ester solvent (for example, ethyl acetate), at a temperature ranging from −20° C. to +40° C., preferably between −5° C. and +25° C., in the presence of an inorganic base (for example, sodium bicarbonate, etc.) or an organic base (for example, triethylamine, pyridine, etc.). Operating under these conditions, products are obtained with a higher ratio D/S isomers than that obtained operating according to the known method described in "Pesticide Science (1985)", Vol. 16, pages 277–286, which consists in reacting N-xylyl-D-methyl alaninate having formula (V) with the chloride of phenylacetic acid in the presence of toluene, at a temperature of 80° C., without bases.

In fact operating according to this method, products are obtained with a satisfactory ratio D/S isomers only after repeated crystallizations which cause considerable reductions in the yield.

The methyl ester having general formula (III), can be conveniently prepared starting from aminoacid alanine, by diazotization of the amine group in the presence of a halide ion as described, for example, in "Methoden der Organischen chemie—Band V/4—Halogen Verbindungen" (1960), page 458, obtaining the corresponding halogenated acid having general formula (VI):

(VI)

wherein X has the same meaning described above, which is subsequently esterified to obtain methyl ester having general formula (III) according to any of the usual known methods in organic practice.

When X, in the methyl ester having general formula (III), represents an activated ester, said methyl ester having general formula (III), is conveniently obtained from methyl lactate, a compound which is commercially available at a low cost, by reaction with a suitable derivative of methanesulfonic, paratoluenesulfonic, trifluoromethanesulfonic acids such as, for example, a chloride or an anhydride, in the presence of or without an organic base such as, for example, triethylamine, N-methylmorpholine, pyridine, or an inorganic base such as, for example, sodium bicarbonate.

The xylidine having formual (IV) is a compound which is commercially available.

Alternatively, the above process can be modified by carrying out the condensation of xylidine having formula (IV), described above, with an acid such as, for example, S-bromo propionic acid having formula (VII):

(VII)

to obtain N-aryl-D-aminoacid having formula (VIII):

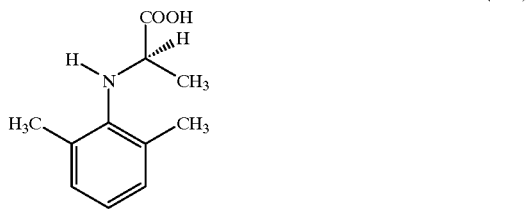

(VIII)

which is subsequently esterified with methanol (CH$_3$OH) in an acid environment by the addition, for example, of hydrochloric acid or sulfuric acid, operating at a temperature ranging from 20° C. to the boiling point of the solution, obtaining N-xylyl-D-methyl alaninate having formula (V) described above. Or, the N-arylaminoacid having formula (VIII) can be acylated with the chloride of phenylacetic acid, operating under the same conditions described in step (b) of the process described above for the acylation of N-xylyl-D-methyl alaninate having formula (V), or operating in an aqueous environment made basic with inorganic bases such as, for example, sodium bicarbonate or sodium hydroxide, possibly in the presence of an organic cosolvent such as, for example, methylene chloride, ethyl acetate, or tetrahydrofuran, operating at a temperature ranging from 0° C. to 20° C., obtaining the acid having formula (IX):

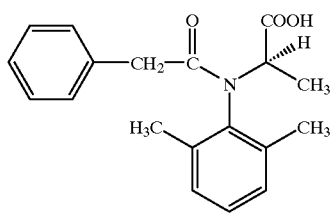

(IX)

which is subsequently transformed into (N-phenylacetyl-N-2,6-xylyl)-methyl alaninate having formula (I), by esterification with methanol, in the presence of acids such as, for example, hydrochloric acid or sulfuric acid, operating at a temperature ranging from 20° C. to the boiling point of the solution.

S-bromo propionic acid having formula (VII) is a product which is commercially available.

A further process which can be used for the preparation of the compound having formula (I) consists in partially hydrolyzing the compound (N-phenyl-acetyl-N-2,6-xylyl)-DL-methyl alaninate (in racemic form), in the presence of enzymes. Depending on the type of enzyme used, the compound having formula (I) can be obtained in its acid form which can be subsequently transformed into the desired compound having formula (I) operating according to the usual methods described in literature. Or, the laevorotatory compound having formula (I) contained in the racemic product is preserved, whereas the dextrorotatory compound having formula (I) is hydrolyzed to acid.

The above hydrolysis reactions can be carried out both in the presence of inert organic solvents such as, for example, chloroform, ethyl acetate, dioxane, and in water maintained at a constant pH by the addition of suitable quantities of inorganic salts to obtain buffer systems. The temperature is maintained at −10° C. to +40° C., care being taken not to select temperatures which cause denaturation of the enzymes used. The above enzymatic-type reaction can also be carried out on N-xylyl-DL-methyl alaninate to obtain N-xylyl-D-methyl alaninate having formula (V), which is subsequently transformed into the compound having formula (I) operating as described in step (b) of the process described above.

The acid or dextrorotatory ester, obtained with the method described above, can be subsequently racemized in basic environments and then subjected to further enzymatic treatment.

Another process which can be used for the preparation of the compound having formula (I) consists in salifying N-xylyl-DL-methyl alaninate with an enantiomerically pure acid such as, for example, tartaric acid or camphorsulfonic acid. The salt thus obtained can give, by fractionated crystallization, the salt corresponding to N-xylyl-D-methyl alaninate in an enantiomerically pure or enriched form. The salification reaction takes place in the presence of solvents such as, for example, halogenated solvents (methylene chloride, etc.), aliphatic esters (ethyl acetate, etc.), aromatic solvents (toluene, etc.), or their mixtures. Further possible recrystallizations followed by treatment of the salified form with basic aqueous solutions, allow the production of N-xylyl-D-methyl alaninate having formula (V), which is then transformed into the compound having formula (I) operating according to what is described in step (b) of the above process.

Alternatively, (N-phenylacetyl-N-2,6-xylyl)methyl alaninate having formula (I) can be obtained by condensation of methyl pyruvate having formula (X):

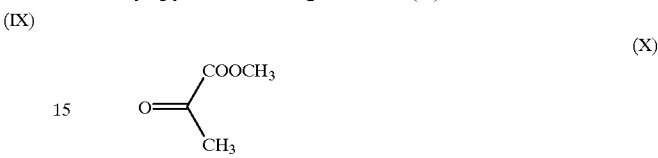

(X)

with the xylidine having formula (IV) described above, in the presence of or without solvents such as, for example, toluene, ethyl acetate, ethyl alcohol, in the presence of or without dehydrating agents such as, for example, anhydrous sodium sulfate and molecular sieves, operating at a temperature ranging from 20° C. to the boiling point of the solution, to obtain the ester N-xylylmethylpropenoate having formula (XI):

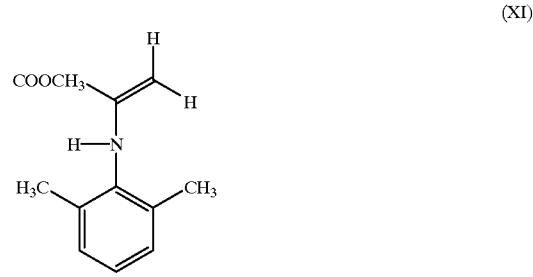

(XI)

which is condensed with the chloride of phenylacetic acid, in the presence of or without an organic base such as, for example, triethylamine, N-methyl-morpholine, pyridine, or an inorganic base such as, for example, sodium bicarbonate, in the presence of an organic solvent such as, for example, methylene chloride, ethyl acetate, toluene, xylene, and in the presence of or without a catalyst such as, for example, N,N-dimethylformamide, operating at a temperature ranging from −20° C. to the boiling point of the solution, obtaining the ester (N-phenylacetyl-N-2,6-xylyl)-methyl propenoate having formula (XII):

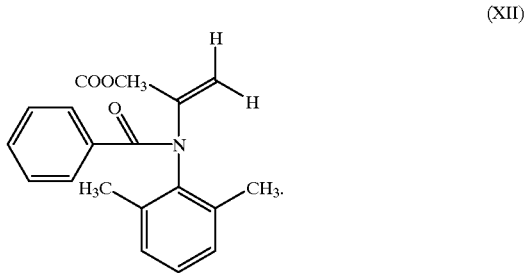

(XII)

The ester (N-phenylacetyl-N-2,6-xylyl)methyl propenoate having formula (XII) is then reduced by catalytic hydrogenation in the presence of a metal such as, for example, ruthenium, palladium, rhodium, platinum, and a chiral inducer such as, for example, a phosphorated derivative such as, for example, 2,2'-bis-(diphenylphosphine)-1,1'-dinaphthyl (known under the trade-name of BINAP) or chiral aminic chelating agents, and in the presence of an alcohol solvent such as, for example, methanol, ethanol, or an organic solvent such as, for example, hexane, cyclohexane, ethyl acetate, toluene, dioxane, or a dipolar aprotic solvent such as, for example, N,N-dimethylformamide, N-methyl-pyrrolidone, operating at a temperature ranging from 20° C. to 150° C. and at a hydrogen pressure ranging from 1 atm to 30 atms, obtaining N-phenylacetyl-N-xylyl)methyl alaninate having formula (I).

Compound (I) is described in "The Pesticide Manual" (1983), VIIth edition, The British Crop Protection Council Ed., page 148.

Compound (2) is described in "The Pesticide Manual" (1983), VIIth edition, The British Crop Protection Council Ed., page 294.

Compound (3) is described in English patent GB 1.500.581.

Compound (4) is described in English patent GB 2.058.059.

Compound (5) is described in "Phytopatological News 12" (1978), Vol. 9, page 142.

Compound (6) is described in European patent application EP 31.257.

Compound (7), also known under the experimental code of ICIA5504, is described in European patent application EP 382.375, and its agronomical properties are specified in "Acts of the Brighton Crop Conference" (1992), pages 435–442.

Compound (8), also known under the experimental code of BASF490S, is described in European patent application EP 253.213.

Compound (9), also known under the experimental code of SSF129 and compound (10), also known under the experimental code of SSF126, are described in Americal U.S. Pat. No. 5,185,242.

Compounds (11)–(15) are described in European patent applications EP 610.764 and EP 550.788.

Specific examples of compounds (16), having general formula (VII), which can be used for the purpose of the present invention are:

manganese ethylenebis (dithiocarbamate) complexed with zinc salts, known as Mancozeb, described in "The Pesticide Manual" (1983), VIIth edition, The British Crop Protection Council Ed., page 339;

manganese ethylenebis(dithiocarbamate), known as Maneb, described in "The Pesticide Manual" (1983), VIIth edition, The British Crop Protection Council Ed., page 340;

zinc ethylenebis(dithiocarbamate), known as Zineb, described in "The Pesticide Manual" (1983), VIIth edition, The British Crop Protection Council Ed., page 564.

Compound (17) is described in "The Pesticide Manual" (1983), VIIth edition, The British Crop Protection Council Ed., page 534.

Compound (18) is described in "The Pesticide Manual" (1983), VIIth edition, The British Crop Protection Council Ed., page 469.

Compound (19) is described in "The Pesticide Manual" (1983), VIIth edition, The British Crop Protection Council Ed., page 17.

Compound (20) is described in "The Pesticide Manual" (1983), VIIth edition, The British Crop Protection Council Ed., page 175.

Compound (21) is described in "The Pesticide Manual" (1983), VIIth edition, The British Crop Protection Council Ed., page 537.

Compound (22) is described in "The Pesticide Manual" (1983), VIIth edition, The British Crop Protection Council Ed., page 87.

Compound (23) is described in "The Pesticide Manual" (1983), VIIth edition, The British Crop Protection Council Ed., page 599.

Compound (24) is described in "The Pesticide Manual" (1983), VIIth edition, The British Crop Protection Council Ed., page 120.

Compound (25) is described in European patent application EP 219.756.

Compound (26) is described in European patent applications EP 360.701 and EP 611.232.

Compound (27) is described in "The Pesticide Manual" (1983), VIIth edition, The British Crop Protection Council Ed., page 225.

Compound (28) is described in European patent application EP 234.242.

Compound (29) is described in English patent GB 1.522.657.

Compound (30) is described in American U.S. Pat. No. 3,912,752.

Compound (31) is described in German patent DE 2.324.010.

Compound (32) is described in German patent DE 2.324.010.

Compound (33) is described in "The Pesticide Manual" (1983), VIIth edition, The British Crop Protection Council Ed., page 252.

Compound (34) is described in "The Pesticide Manual" (1983), VIIth edition, The British Crop Protection Council Ed., page 422.

Compound (35) is described in "The Pesticide Manual" (1983), VIIth edition, The British Crop Protection Council Ed., page 314.

Compound (36) is described in "The Pesticide Manual" (1983), VIIth edition, The British Crop Protection Council Ed., page 473.

Compound (37) is described in "The Pesticide Manual" (1983), VIIth edition, The British Crop Protection Council Ed., page 461.

Compounds (38) such as, for example, copper oxychloride, copper oxide (I) or (II), copper chloride hydroxide, copper sulfate, can be easily found on the market.

Compound (39) is described in "$17^{th}$ International Congress of Pesticide Chemistry" (1990), Abstract, Hamburg, page 227.

Compound (40) is described in "Brighton Crop Protection Conference—Pests and Diseases" (1996), Atti del Congresso.

Compound (41) is described in European patent application EP 629.616.

Compounds (42) are described in "Pesticide Science" (1996), Vol. 47, pages 191–197.

Compounds (43) are described in European patent application EP 572.191.

Compounds (44) are described in European patent application EP 753.258.

Compounds (45) are described in European patent application EP 652.299.

Compound (46) is described in American U.S. Pat. No. 4,931,581.

Preferred fungicidal compositions for the purposes of the present invention are those comprising, as well as the compound having formula (I):

Mancozeb;

Mancozeb and Fosetil;

Mancozeb and Cimoxanil;

Fosetil;

Fosetil and Cimoxanil;

Propamocarb corresponding to propyl 3-(dimethylamino)propylcarbamate;

Chlorothalonil;

a salt of copper (I) or copper (II);

a salt of copper (I) or copper (II) and Fosetil;

a salt of copper (I) or copper (II) and Cymoxanil;

Dimethomorph;

Flumetover;

methylbenzothiadiazole-7-thiocarboxylate;

one of the following compounds included in the general formula specified in point (43):
- 1-(3-iodine-2-propinyl)-3-(3,5-dichlorophenyl)-5-methylhydantoine;
- 1-(3-iodine-2-propinyl)-3-(4-chlorophenyl)-5-methylhydantoine;
- 1-(3-iodine-2-propinyl)-3-(4-fluorophenyl)-5-methylhydantoine;
- 1-(3-iodine-2-propinyl)-3-(3,5-dichlorophenyl)-5,5-spiro-cyclopentanhydantoine;
- 1-(3-iodine-2-propinyl)-3-(3,5-dichlorophenyl)-5,5-spiro-cyclohexanhydantoine;
- 1-(3-iodine-2-propinyl)-3-(3,5-dichlorophenyl)-5,5-dimethylhydantoine;

one of the following compounds included in the general formula specified in point (44):
- N-[3'-(1'-chloro-3'-methyl-2'-oxopentane)]-3,5-dichloro-4-methylbenzamide;
- N-[3'-(1'-chloro-3'-methyl-2'-oxopentane)]-3,5-dichloro-4-ethylbenzamide;
- N-[3'-(1'-chloro-3'-methyl-2'-oxopentane)]-3,5-dichloro-4-ethoxybenzamide;
- N-[3'-(1'-chloro-3'-methyl-2'-oxopentane)]-3,5-dichloro-4-methoxybenzamide;
- N-[3'-(1'-chloro-3'-methyl-2'-oxopentane)]-3,5-dichloro-4-cyanobenzamide;
- N-[3'-(1'-chloro-3'-methyl-2'-oxopentane)]-3,5-dibromo-4-methylbenzamide;

one of the following compounds included in the general formula specified in point (45):
- S-R-3-[N-(N-isopropoxycarbo nylvalinyl)amino]-3-isopropyl phenylpropanoate;
- S-RS-3-[N-(N-isopropoxycarbonylvalinyl)amino]-3-isopropyl phenylpropanoate.

The fungicidal compositions of the present invention have a high fungicidal activity with respect to Oomycetes. Examples of pathogens controlled by the above compositions, together with examples of application crops, are provided below:

*Plasmopora viticola* (vine);
*Phytophthora infestans* (tomato, potato);
*Phytophthora nicotianae* (tobacco, ornamental plants, etc.)
*Phytophthora palmivora* (cacao, etc.)
*Phytophthora cinnamoni* (pineapple, cedar, lemon, tomato, etc.)
*Phytophthora capsici* (pepper, tomato, cucurbitaceae, etc.)
*Phytophthora cryptogea* (tomato, thorn-bush, ornamental plants, etc.)
*Phytophthora megasperma* (ornamental plants, etc.)
*Peronospora tabacina* (tobacco);
*Pseudoperonospora cubensis* (cabbage, cucurbitaceae);
*Pseudoperonospora humuli* (hop);
*Phythium ultimum* (various crops); etc.

The fungicidal compositions of the present invention can be prepared by mixing each compound using the following doses per hectare.

5–500 g of compound having formula (I);

5–3500 g of each fungicide from (1) to (46).

The fungicidal compositions of the present invention are capable of carrying out a fungicidal activity of both a curative and preventive nature and they also have a limited or no phytotoxicity.

The above compositions can be applied to any part of the plant, to both the aerial parts (leaves, stems, shoots, branches) and also the hypogeous parts for controlling typical root pathogens, or to the seeds before planting, or even to the earth where the plant grows.

Compositions can be used which are in the form of dry powders, wettable powders, emulsifiable concentrates, microemulsions, pastes, granulates, solutions, suspensions, etc: the selection of the type of composition will depend on its specific use.

The compositions are prepared in the known way, for example by diluting or dissolving the active substances with a solvent medium and/or solid diluent, possibly in the presence of surface-active agents.

Solid diluents, or carriers, which can be used are: silica, kaolin, bentonite, talc, infusorial earth, dolomite, calcium carbonate, magnesia, chalk, clays, synthetic silicates, attapulgite, sepiolite.

Liquid diluents which can be used, apart from water obviously, are various solvents, for example aromatics (xylols or mixtures of alkylbenzols), chloroaromatics (chlorobenzol), paraffins (petroleum fractions), alcohols (methanol, propanol, butanol, octanol, glycerine), amines, amides (N,N-dimethylformamide, N-methylpyrrolidone), ketones (cyclohexanone, acetone, acetophenone, isophorone, ethylamylketone), esters (isobutyl acetate).

Surface-active agents which can be used are salts of sodium, calcium, triethanolamine or triethylamine of alkylsulfonates, alkylarylsulfonates, polyethoxylated alkylphenols, fatty alcohols condensed with ethylene oxide, polyoxyethylated fatty acids, polyoxyethylated sorbitol esters, ligninsulfonates.

The above compositions can also contain special additives for particular purposes such as, for example, adhesion agents, such as wattle gum, polyvinyl alcohol, polyvinylpyrrolidone.

If desired, it is possible to also add other compatible active principles to the compositions of the present invention, such as, for example, other fungicides, phytoregulators, antibiotics, herbicides, insecticides, fertilizers.

Examples of fungicides which can be included in the composition of the invention are alanicarb, ampropylfos, azaconazole, azoxystrobin, BAY KTU 3616, benomyl, biloxazol, binapacryl, blasticidine S, bromoconazole, bupyrimate, butenaclor, butiobate, captafol, carbendazim, carboss, quinoethionate, chlorobenzothiazone, chloroneb, clozolinate, clozylacon, copper salts, cyclohexylimide, cyproconazole, cyprofuran, CGA 245 704, diclone diclobutrazole, diclomezine, dicloran, didecyl- or dimethyl-ammonium chloride, dietofencarb, difeconazole, dimefluazole, dimethconazole, dimethirimol, diniconazole, dinocap, dipyrithione, ditalimfos, dodemorf, dodine, doguadine, edifenfos, epoxyconazole, etaconazole, etirimol, ethoxyquin, fenaminosulf, fenapanil, fenarimol, phenbuconazole, phenfuran, phenpiclonil, phenpropidine, fenpropimorf, fentin acetate, ferbam, ferimzone, fludioxonyl, fluoroimide, fluotrimazole, flutolanil, flutriafol, fluzilazol, fuberidazole, furalaxyl, cis-furconazole, guazatine, ICI A 5504, hydroxyiso-oxazol, imazalil, imibenconazole, ipconazole, iprobenfos, iprodione, isoprotiolane, kasugamicine, kresoximethyl, mancozeb, maneb, mepronil, metconazole, metfuroxam, metiram, metsulfovax, myclobutanil, neoasozin, nuarimol, oxycarboxyn, perfurazoate, penconazole, phenazine oxide, phosphoric acids, phthalide, polyoxin D, polyram, probenazole, procloraz, procimidone, propionic acid, piracarbolid, pyrazofos, pyrimethanyl, pyriphenox, pyroquilon, pyroxyfur, pyrrolnitrin, compounds containing quaternary ammonium, quinconazole, quinomethionate, quintozene, rabenazole, sodium pentachlorophenate, SSF 126, SSF 129, spiroxamine, streptomycine, sulfur, tebuconazole, teclophthalam, tecnazene, thiabendazole, ticarbanil, ticiophen, thifluzamide, 2-(thiocyanomethylthio) benzothiazole, methyl-thiophanate, timibenconazole, methyl-ticlophos, triacetate salt of 1,1'-imino-di-(octamethylene) diguanidine, triazabutyl, triazaoxide, tricyclazole, tridemorf, triforine, triflumizole, trithiconazole, validamycine A, vapam, vinclozolin, zineb and ziram.

The concentrations of the active substances in the above compositions can vary within a wide range, depending on the crop, pathogen, environmental conditions and the type of formulation adopted.

The concentration of the active substances generally varies from 0.1% to 95%, preferably from 0.5% to 90%.

When the above fungicidal compositions are applied to the leaves, a dose equal to 5–350 g/hl of each active principle is preferably used for the treatment of fruit crops whereas a dose equal to 80–3500 g/ha of each active principle is preferably used for the treatment of extensive crops (potato, hop, etc.).

When the above fungicidal compositions are applied to the seed, overall doses of active principles equal to 0.0001–30 g per kilogram of seeds, are used.

The synergetic effect of compound (a) can also be observed when compounds (a) and (b) are applied separately to the plant to be treated instead of being mixed with each other, as occurs in the above compositions in which compound (a) is mixed with one or more fungicides selected from the compounds cited in points 1 to 46. The present invention therefore also relates to a method for controlling phytopathogen fungi in a plant which comprises the application of:

an effective quantity of compound (a); and
an effective quantity of one or more fungicides (b); to the seeds, leaves, roots, or earth where the plant grows.

The following examples provide an illustration of the present invention but do not limit its scope. In the examples, the synergetic effect of the components of the mixture can be seen by comparing the experimental data with the theoretical efficiency of the fungicidal composition of the present invention, calculated according to the Limpel formula ("Pesticide Science" (1987), Vol. 19, pages 309–315:

$$E = x + y - xy/100$$

wherein:
E is the fungicidal activity expected, without synergetic effects, from a composition obtained by mixing g.x of compound X with g.y of compound Y;
x is the activity of compound X when used alone at the dose g.x;
y is the activity of compound Y when used alone at the dose g.y.

When the fungicidal activity experimentally obtained, is higher than the value of E, this activity is considered as being synergetic effect.

EXAMPLE 1

($A_1$) Preparation of N-xylyl-D-methyl alaninate.

13.5 g of 2,6-xylidine (Aldrich) are added to 16.7 g of methyl S-bromopropionate obtained by esterification of the corresponding Aldrich acid esterified with methanol under acid conditions, and the mixture is heated for 3 hours, at a temperature of 110° C. The raw material obtained is directly purified on silica gel, using a mixture of hexane and ethyl acetate in a ratio of 7/3 v/v, as eluant.

16.3 g of N-xylyl-D-methyl alaninate are obtained (yield 79%).

($A_2$) Preparation of N-xylyl-D-methyl alaninate.

N-xylyl-D-methyl alaninate is also obtained by operating with an analogous process to that described above in ($A_1$) using methyl S-2-tosyloxypropionate or methyl S-mesyloxypropionate in substitution of methyl S-bromopropionate, obtaining 82% and 85% yield, respectively.

($B_1$) Preparation of (N-phenylacetyl-N-2,6-xylyl)-D-methyl alaninate having formula (II).

A solution of 98 g of N-xylyl-D-methyl alaninate, obtained as described above and 91.4 g of phenylacetic acid chloride in 1200 cm$^3$ of toluene, is heated to reflux temperature, for 2 hours, in the presence of 2.5 cm$^3$ of dimethylformamide.

After cooling, the solution obtained is washed with aqueous bicarbonate and the organic phase is evaporated at reduced pressure after drying with sodium sulfate.

The raw material thus obtained (158 g) is crystallized with abundant hexane obtaining 114 g of a white crystalline solid corresponding to (N-phenylacetyl-N-2,6-xylyl)methyl alaninate with an enantiomeric D/S ratio=80/20. This white solid is recrystallized three times with a mixture of hexane/ethyl acetate in a ratio 95/5 obtaining decreasing quantities of (N-phenylacetyl-N-2,6-xylyl)methyl alaninate progressively enriched with the desired D isomer:
1st crystallization: 90.0 g (yield of 60%), D/S ratio=88/12;
2nd crystallization: 61.4 g (yield of 40%), D/S ratio=94/6;
3rd crystallization: 25.8 g (yield of 16.8%), D/S ratio=98.5/1.5.

The above enantiomeric ratios are determined with a CHIRALCEL OD chiral column (10 μm–4.6×250 mm), eluating with a mixture of hexane/isopropyl alcohol in a ratio 7/3, at a flow-rate of 0.5 ml/minute.

($B_2$) Preparation of (N-phenylacetyl-N-2,6-xylyl)-D-methyl alaninate having formula (II).

42 g of sodium bicarbonate are added to a solution of 100 g of N-xylyl-D-methyl alaninate in 500 cm$^3$ of toluene, cooled to a temperature ranging from 5° C. to 10° C., and subsequently 75 g of phenylacetic acid chloride are slowly added dropwise.

After 4 hours at room temperature, the above solution is washed with water and then evaporated at reduced pressure after drying with sodium sulfate. The raw material thus obtained is crystallized with abundant hexane obtaining 106 g of a white crystalline solid corresponding to (N-phenylacetyl-N-2,6-xylyl)-methyl alaninate with an enantiomeric D/S ratio=98/2 (yield 92.5%).

($B_3$) Preparationof (N-phenylacetyl-N-2,6-xylyl-D-methyl alaninate having formula (II).

15.5 g of phenylacetic acid chloride are added to a solution of 20.7 g of N-xylyl-D-methyl alaninate, obtained as described above, in 100 cm³ of toluene. After 4 hours at reflux temperature, the reaction is cooled, evaporated at reduced pressure and the raw material obtained is purified on silica gel, using a mixture of hexane and ethyl acetate in a ratio 7/3 v/v, as eluant.

28.9 g of (N-phenylacetyl-N-2,6-xylyl-D-methyl alaninate having formula (II) are obtained, with an $([\alpha]_D$ rotatory optical power of −27.3° (c=1, acetone) (yield 89%).

EXAMPLE 2

Analogously to what is described in Example 1, but starting from methyl R-bromopropionate, (N-phenylacetyl-N-2,6-xylyl-D-methyl alaninate having formula (II), is obtained, in two passages, with an $([\alpha]_D$ rotatory optical power of +27.4° (c=1, acetone) (yield 89%).

EXAMPLE 3

Synergetic effects of fungicidal compositions containing (N-phenyl-acetyl-N-2,6-xylyl)-D-methyl alaninate and Dimethomorph in the control of infections caused by *Plasmopara viticola* on vines.

Leaves of cultivar Dolcetto vine plants grown in vases in a conditioned environment (20±1° C.), 70% relative humidity) are treated by spraying both sides with hydroacetonic solutions at 20% by volume of acetone of the following compositions (the proportions of the components are indicated in Table 1):

(N-phenyl-acetyl-N-2,6-xylyl)-D-methyl alaninate (A) and Dimethomorph (B) [fungicide indicated above under point (25)];

(N-phenyl-acetyl-N-2,6-xylyl)methyl alaninate raceme (C) and Dimethomorph (B) [fungicide indicated under point (25)].

After remaining 24 hours in a conditioned environment, the plants were sprayed on both sides of the leaves with an aqueous suspension of conidia of *Plasmopora viticola* (200000 conidia per cm³).

The plants were maintained in a humidity saturated environment, at 21° C., for the incubation period of the fungus.

At the end of this period (7 days), the gravity of the attack is estimated and the defence percentage is calculated according to the following formula:

$$D = (1 - lm_1/lm_0) * 100$$

wherein $lm_1$ is the disease index of the plants treated and $lm_0$ is that of the plants not treated (references).

The synergetic effect is obtained from the ratio between the activity experimentally observed and that calculated according to the Limpel formula described above.

The data obtained are indicated in Table 1.

EXAMPLE 4

Synergetic effects of fungicidal compositions containing (N-phenyl-acetyl-N-2,6-xylyl)-D-methyl alaninate and S-RS-3-[N-(N-isopropoxycarbonyl-valinyl) amino] isopropyl phenylpropanoate in the control of infections caused by *Plasmopara viticola* on vines.

Using the same method described in Example 3, the following compositions are tested (the proportions of the components are indicated in Table 2):

N-phenyl-acetyl-N-2,6-xylyl)-D-methyl alaninate (A) and S-RS-3-[N-(N-isopropoxycarbonyl-valinyl)-amino]-3-isopropylphenylpropanoate (D) [fungicide included in the general formula indicated above under point (45)].

(N-phenyl-acetyl-A-2,6-xylyl)methyl alaninate raceme (C) and S-RS-3-[N-(N-isopropoxycarbonyl-valinyl) amino]-3-isopropylphenylpropanoate (D) [fungicide included in the general formula indicated above under point (45)].

The data obtained are indicated in Table 2.

EXAMPLE 5

Synergetic effects of fungicidal compositions containing (N-phenyl-acetyl-N-2,6-xylyl)-D-methyl alaninate mixed with the compounds Flumetover (compound 26) and Famoxadone (compound 40) in the control of infections caused by *Plasmopara viticola* on vines.

Using the same method described in Example 3, the following compositions are tested:

(N-phenyl-acetyl-N-2,6-xylyl)-D-methyl alaninate (A) and Flumetover (E)

(N-phenyl-acetyl-N-2,6-xylyl)-DL-methyl alaninate (C) and Flumetover (E)

The data obtained are indicated in table 3.

(N-phenyl-acetyl-N-2,6-xylyl)-D-methyl alaninate (A) and Famoxadone (F)

(N-phenyl-acetyl-N-2,6-xylyl)-DL-methyl alaninate (C) and Famoxadone (F)

The data obtained are indicated in table 4.

EXAMPLE 6

Synergetic effects of fungicidal compositions containing (N-phenyl-acetyl-N-2,6-xylyl)-D-methyl alaninate mixed with Fosetyl Alumino (compound 2) or mixed with Fosetyl Alumino (compound 2) and Mancozeb (compound 16) or mixed with copper hydroxide (compound type 38) in the control of infections caused by *Plasmopara viticola* on vines.

Three-year old cv. Barbera vines were treated with applications of (N-phenyl-acetyl-N-2,6-xylyl)methyl alaninate mixed with Fosetyl alumino (compound 2) or mixed with Fosetyl alumino (compound 2) and Mancozeb compound 16) or mixed with copper hydroxide (compound type 38) at intervals of 12–15 days according to appropriate agronomical practice. In particular a comparison was made of mixtures containing (N-phenylacetyl-N-2,6-xylyl)methyl alaninate both in its optically active D form (Compound A) and in its racemic DL form (Compound C). After 3 applications, after observing a significant leaf infection in the reference (72.5%), observation was made of the damage in the parcels treated. The effectiveness was evaluated as control percentage of the disease with respect to the damage observed on the vines which had not been treated, determining the average percentage of damage of 100 leaves. Considering the proven identical activity of a half dose of compound (A) with respect to the full dose of (C), the differences in effectiveness indicated in tables 5–7 can therefore be attributed to the different and greater synergetic effect shown by form D (Compound A) mixed with the partners used.

TABLE 1

| | (A) or (C) concentration | Concentration of (B) (ppm) | Limpel expected activity (%) | Activity observed | Activ. obser./ activ. calcul. |
|---|---|---|---|---|---|
| (C) | 0.20 | — | — | 35.0 | — |
| (A) | 0.10 | — | — | 36.0 | — |
| — | — | 0.40 | — | 30.0 | — |

TABLE 1-continued

| (A) or (C) concentration | Concentration of (B) (ppm) | Limpel expected activity (%) | Activity observed | Activ. obser./activ. calcul. |
|---|---|---|---|---|
| (C) 0.20 | 0.40 | 54.5 | 59.5 | 1.10 |
| (A) 0.10 | 0.40 | 55.0 | 69.0 | 1.25 |

TABLE 2

| (A) or (C) concentration | Concentration of (B) (ppm) | Limpel expected activity (%) | Activity observed | Activ. obser./activ. calcul. |
|---|---|---|---|---|
| (C) 0.20 | — | — | 35.0 | — |
| (A) 0.10 | — | — | 38.0 | — |
| — | 1.80 | — | 15.0 | — |
| (C) 0.20 | 0.40 | 45.0 | 52.0 | 1.15 |
| (A) 0.10 | 0.40 | 45.5 | 61.0 | 1.35 |

TABLE 3

| (A) or (C) concentration | Concentration of (E) (ppm) | Limpel expected activity (%) | Activity observed | Activ. obser./activ. calcul. |
|---|---|---|---|---|
| (C) 0.20 | — | — | 35.0 | — |
| (A) 0.10 | — | — | 36.0 | — |
| — | 0.15 | — | 28.0 | — |
| (C) 0.20 | 0.15 | 53.2 | 60.1 | 1.13 |
| (A) 0.10 | 0.15 | 53.9 | 69.5 | 1.29 |

TABLE 4

| (A) or (C) concentration | Concentration of (F) (ppm) | Limpel expected activity (%) | Activity observed | Activ. obser./activ. calcul. |
|---|---|---|---|---|
| (C) 0.20 | — | — | 35.0 | — |
| (A) 0.10 | — | — | 36.0 | — |
| — | 0.10 | — | 20.0 | — |
| (C) 0.20 | 0.10 | 48.0 | 56.6 | 1.13 |
| (A) 0.10 | 0.10 | 48.8 | 63.9 | 1.31 |

TABLE 5

Activity of mixtures of (N-phenyl-acetyl-N-2,6-xylyl)methyl alaninate with Fosetyl Aluminum (compound 2)

| Product | (A) or (C) concentration (g/hl) | Product (2) concentration (g/hl) | Activity observed |
|---|---|---|---|
| (A) | 10 | 160 | 99.9 |
| (C) | 20 | 160 | 97.5 |

TABLE 6

Activity of mixtures of (N-phenyl-acetyl-N-2,6-xylyl)methyl alaninate with Fosetyl Aluminum (compound 2) and Mancozeb (compound 16)

| Product | (A) or (C) concentration (g/hl) | Products (2) and (16) concentrations (g/hl) | Activity observed |
|---|---|---|---|
| (A) | 5 | 140 + 140 | 99.9 |
| (C) | 10 | 140 + 140 | 98.2 |

TABLE 7

Activity of mixtures of (N-phenyl-acetyl-N-2,6-xylyl)methyl alaninate with copper hydroxide (compound like 38)

| Product | (A) or (C) concentration (g/hl) | Product (2) concentration (g/hl) | Activity observed |
|---|---|---|---|
| (A) | 10 | 100 | 99.2 |
| (C) | 20 | 100 | 98.6 |

EXAMPLE 7

Activity "in vitro" on *Phythium ultimum*.

(N-phenylacetyl-N-2,6-xylyl)-D-methyl alaninate having formula (II) obtained as described above, (N-phenylacetyl-N-2,6-xylyl)-L-methyl alaninate and (N-phenylacetyl-N-2,6-xylyl)-DL-methyl alaninate (Benalaxyl) are incorporated in an agarized culture medium, at a temperature of 50° C., which is distributed into Petri capsules with a diameter of 55 mm. After solidification of the agarized medium, the capsules are inoculated by placing in the centre a disk having a diameter of 6 mm of of agar supporting the mycelium of the fungus under examination (*Phythium ultimum*).

After 5 days of conservation at 28° C., the diameter of the colony which has developed is measured and is related to the diameter of a colony cultivated on non-treated medium.

On the basis of these measurements the percentage of growth inhibition is calculated according to the formula:

$$I=(1-d_1/d_0)*100$$

wherein $d_1$ is the diameter of the treated colony and $d_0$ that of the non-treated colony.

The above laevorotatory (D), dextrorotatory (L) and racemic (DL) compounds are tested at different concentrations to establish the minimum quantity capable of inhibiting 50% of myceliary growth (MIC). The data obtained are indicated in Table 8.

TABLE 8

| FORM | MIC (ppm) |
|---|---|
| D | 0.05 |
| DL | 0.20 |
| L | 40.00 |

EXAMPLE 8

Determination of the residues of active principle in hops.

Small hop plants are treated with six leaf applications of (N-pehnylacetyl-N-2,6-xylyl-D-methyl alaninate having formula (II) obtained as described above, or N-phenylacetyl-N-2,6-xylyl-DL-methyl alaninate (Benalaxyl), at a dose of 450 g/ha, at intervals of 10–15 days.

Samples of hops, equal to about 1 kg of humid vegetable, are removed after carrying out the last treatment ($T_0$) and subsequently after 1 day ($T_1$) and after three days ($T_3$).

Each sample is homogenized and ground with acetone. The suspension obtained is then filtered on glass fibre (GF/C W Whatman) under vacuum. The liquid phase is evaporated and the aqueous residue obtained is extracted with methylene chloride.

The organic phase is concentrated and the organic extract thus obtained is purified on alumina, eluating with hexane/acetone in a ratio 90/10. The fractions containing the active principle are collected, which are subsequently evaporated and ethylene acetate is added up to a known volume. The content of active principle is then determined by means of gas-chromatographic analysis (GLC/FID; "alkaline flame ionization detector) with respect to an external standard and referring to the original sample.

The averages of the data obtained are indicated in Table 9 wherein (D) indicates the laevorotatory compound and (DL) indicates the raceme.

TABLE 9

RESIDUES OF ACTIVE PRINCIPLE (D) OR (DL) IN SAMPLES OF HOPS (mg/kg)

| DAY OF COLLECTION OF SAMPLE | RESIDUE OF COMPOUND (DL) | RESIDUE OF COMPOUND (D) |
| --- | --- | --- |
| $T_0$ | 3.070 | 2.990 |
| $T_1$ | 2.717 | 2.513 |
| $T_2$ | 1.358 | 0.980 |

What is claimed is:

1. A fungicidal composition, comprising:
   (a) A compound, which is (N-phenylacetyl-N-2,6-xylyl) methyl alaninate, having the formula (I):

(I)

wherein more than 50% of said compound having the formula (I) consists of the levorotatory enantiomer; and
   (b) one or more fungicided compounds selected from the group consisting of
   (1) Cymoxanil, which is 1-(2-cyano-2-methoxyiminoacetyl)-3-ethyl-urea;
   (2) Fosetyl, having the formula:

$$\left[ CH_3CH_2O-\overset{O}{\underset{H}{P}}-O^- \right]_3 Al^{3+};$$

(3) Metalaxyl, which is methyl-N-(2-methoxyacetyl)-N-2,6-xylyl-DL-alaninate;
   (4) Oxadixyl, which is 2-methoxy-N-(2-oxo-1,3-oxazolidin-3-yl)-acet-2'-6'-xylidine;
   (5) Ofurace, which is DL-3-[N-chloroacetyl-N-(2,6-dimethylphenyl)-amino]-γ-butyrolactone;
   (6) Fluazinam, which is 3-chloro-N-[3-chloro-2,6-dinitro-4-(trifluoromethyl)-phenyl]-5-trifluoromethyl-2-2-pyridinamine;
   (7) (E)-2-[2-([6-(2-cyanophenoxy)-pyrimidin-4-yloxy]-phenyl-3-methyl methoxyacrylate;
   (8) (E)-methoxyimino-α-o-tolyloxy)-o-tolyl]-methyl acetate;
   (9) N-methyl-(E)-methoxyimino-[2-(2,5-dimethyl-phenoxymethyl)-phenyl]acetamide;
   (10) N-methyl-(E)-methoxyimino[2-phenoxyphenyl] acetamide;
   (11) O-(1-methylethyl)-N-[2-methyl-1-[[1-(4-chloro-phenyl)ethyl]-amino]-carbonyl]-propyl]-carbamate;
   (12) O-(1-methylethyl)-N-[2-methyl-1-[[[1-(4-methyl-phenyl)ethyl]-amino]-carbonyl]-propyl]-carbamate;
   (13) O-(1-methylethyl)-N-[2-methyl-1-[[[1-(4-ethyl-phenyl)-ethyl]-amino]-carbonyl]-propyl]-carbamate;
   (14) O-(1-methylethyl)-N-[2-methyl-1-[[[1-(4-methoxyphenyl)-ethyl]-amino]-carbonyl]-propyl]-carbamate;
   (15) O-(phenyl)-N-[2-methyl-1-[[[1-(4-methoxyphenyl)-ethyl]-amino]-carbonyl]-propyl]-carbamate;
   (16) dithiocarbamates having the formula:

$$\begin{matrix} H_2C-NH-CS-S \\ | \phantom{XXXXXXXXX} \diagdown \\ \phantom{XXXXXXXXXXX} M \\ | \phantom{XXXXXXXXX} \diagup \\ H_2C-NH-CS-S \end{matrix}$$

wherein M represents manganese or zinc;
   (17) Thiram, which is bis-(dimethyl-t-biocarbamoyl)-disulfide;
   (18) Propineb, having the formula:

$$\left[ -ZN-S-CS-NH-CH_2-\overset{CH_3}{\underset{}{CH}}-NH-CS-S- \right]_n;$$

(19) Anilazine, which is N-(4,6-dichloro-1,3,5-triazin-2-yl)-aniline;
   (20) Dichlofluanid, having the formula:

$$-(CH_3)_2=N-SO_2N-S-CCl_2F;$$

(21) Tolylfluanid, having the formula:

$$-(CH_3)_2-N-SO_2N-S-CCl_2F;$$

(22) Captan, having the formula:

[Structure: tetrahydrophthalimide N–S–CCl₃]

(23) Folpet, having the formula:

[Structure: phthalimide N–S–CCl₃]

(24) Chlorothalonil, which is 1,3-dicyano-2,4,5,6-tetrachlorobenzene;
(25) Dimethomorph, having the formula:

[Structure: 4-chlorophenyl and 3,4-dimethoxyphenyl C=CH–CO–N(morpholine)]

(26) Flumetover, which is N,N-diethyl-amide of 4-trifluoromethyl-6-(3,4-dimethoxyphenyl)-benzoic acid;
(27) Dithianon, which is 5,10-dihydro-5,10-dioxonaphthol-[2,3-b]-1,4-diethin-2,3-dicarbonitrile;
(28) Tetraconazole, which is 1-(1H-1,2,4-triazol-1-yl)-2-(2,4-dichlorophenyl)-3-(1,1,2,2-tetrafluoroethoxy)-propane;
(29) Propiconazole, which is 1-[2-(2,4-dichlorophenyl)-4-propyl-1,3-dixolan-2-yl-methyl]-1H-1,2,4-triazole;
(30) Triadimefon, which is 1-(4-chlorophenoxy)-3,3-dimethyl-1-(1H-1,2,4-triazol-1-yl)-butanone;
(31) Triadimenol, which is 1-(4-chlorophenoxy)-3,3-dimethyl-1-(1H-1,2,4-triazol-1-yl)butan-2-ol;
(32) Bitertanol, which is 1-(diphenyl-4-yloxy)-3,3-dimethyl-1-(1H-1,2,4-triazol-1-yl)-butan-2-ol;
(33) Etridiazole, which is ethyl 3-trichloromethyl-1,2,4-thiadiazolyl ether;
(34) Pencycuron, which is 1-(4-chlorobenzyl)-1-cyclopentyl-3-phenylurea;
(35) Hymexanol, which is 5-methyl-soxazol-3-ol;
(36) Protiocarb, which is S-ethyl-(3-dimethylaminopropyl)-thiocarbamate;
(37) Propamocarb, which is propyl 3-(dimethylamino)-propylcarbamate;
(38) salts of copper (I) or copper (II);
(39) Andoprim; which is 2-p-methoxy-aniline-4,6-dimethyl-pyrimidine;
(40) Famoxadone or DPX-HE874, which is 5-methyl-5-(4-phenoxyphenyl)-3-(phenylamino)-oxazolidin-2,4-dione;
(41) 4-methyl-4-phenyl-1-(phenylamino)-2-methylthio-imidazolidin-5-one;
(42) pyrimidinic compounds;
(43) compounds having the following formula:

[Structure: hydantoin with R₁, R₂, R₃, R₄ substituents]

wherein:
$R_1$ and $R_2$, which are the same or different, each represents hydrogen; or $C_1$–$C_3$ alkyl; or $R_1$ and $R_2$ together with the hydantoinic ring to which they are attached, represent a $C_3$–$C_7$ saturated spiro ring;
$R_3$ and $R_4$, which are different from each other, each represents $C_1$–$C_3$ alkyl; phenyl group, said phenyl group optionally substituted with halogen, nitro, $C_1$–$C_3$ alkoxyl, or $C_1$–$C_3$ haloalkyl; or 3-iodo-propinyl;

(44) compounds having the following formula:

[Structure: R₁, R₂, R₃-substituted benzamide C(=O)–NH–C–C–CH₂X]

wherein
$R_1$ and $R_3$, which are the same or different, each represents halogen; or $C_1$–$C_4$ alkyl;
$R_2$ represents alky; alkenyl; $C_2$–$C_6$ alkinyl; a $C_1$–$C_4$ alkoxyl; cyano;
$R_4$ and $R_5$, which are the same or different; each represents halogen; or $C_1$–$C_4$ alkyl;
with he proviso that at least one between $R_4$ and $R_5$, is alkyl;
X represents halogen, thiocyano, or isothiocyano;
(45) oligopeptidic compounds having the formula:

K—[A]$_z$—[B]$_w$—L wherein
z and w, which are the same or different, are 1 or 2;
A represents an aminoacidic portion having the formula:

[Structure: –N(R')–CH(Ra)–C(=O)–]

wherein:
$R_a$ represents linear or branched $C_3$–$C_4$ alkyl; or $C_3$–$C_4$ cycloalkyl;
R' represents hydrogen; $C_1$–$C_3$ alkyl; or, together with $R_a$ forms a linear or branched $C_3$–$C_5$ alkylene chain;

B represents an aminoacid portion having the formula:

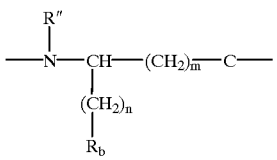

wherein
R_b represents phenyl or an aromatic heterocyclic group, said phenyl and heterocyclic groups, also being optionally substituted;
m and n, which are the same or different, are 0 or 1;
R" represents hydrogen; or $C_1$–$C_3$ alkyl;
L represents a group having the formula:

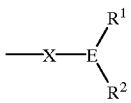

wherein:
E represents a linear or branched $C_1$–$C_8$ alkylene chain; a linear or branched $C_2$–$C_8$ω-oxoalkyl chain; or a direct bond;
$R^1$ represents hydrogen; cycloalkyl; phenyl or an aromatic heterocyclic group; said phenyl and heterocyclic groups also being optionally substituted;
$R^2$ represents hydrogen; linear or branched $C_2$–$C_6$ carboxyalkyl; linear or branched or cyclic $C_2$–$C_6$ carbamoyl; or cyano;
X represents —O—; —N($R^3$)—; or —N($R^4$)—O—; wherein:
$R^3$ represents hydrogen; $C_1$–$C_3$ alkyl or alkoxyl; or, together with $R_1$, represents a direct bond or a linear or branched $C_2$–$C_4$ alkylene chain;
$R^4$ represents hydrogen; $C_1$–$C_3$ alkyl; or, together with $R_1$, represents a direct bond;
K represents hydrogen; linear or branched $C_1$–$C_4$ alkyl; or a protective group having the formula:

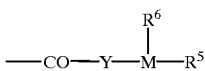

wherein:
Y represents oxygen; or a direct bond;
M represents a linear, branched or cyclic $C_1$–$C_8$ alkylene chain; or a direct bond;
$R^5$ represents hydrogen; phenyl group which is optionally substituted; linear, branched or cyclic $C_2$–$C_6$ carbamoyl; linear, branched or cyclic $C_1$–$C_6$ carboalkoxyl; or cyano;
$R^6$ represents hydrogen; $C_1$–$C_3$ alkoxyl; acetate; or an acetamidic group;
(46) methylbenzothiadiazole-7-thiocarboxylate.

2. The fungicidal composition of claim 1, wherein the compound having the formula (I) contains more than 90% of levorotatory enantiomer.

3. The fungicidal composition of claim 1, wherein the compound having the formula (I) contains more than 95% of levorotatory enantiomer.

4. The fungicidal composition of claim 1, wherein the compound having the formula (I) contains more than 99% of levorotatory enantiomer.

5. The fungicidal composition of claim 1, wherein the fungicide (b) is Mancozeb.

6. The fungicidal composition of claim 1, wherein the fungicide (b) is Mancozeb and Fosetil.

7. The fungicidal composition of claim 1, wherein the fungicide (b) is Mancozeb and Cimoxanil.

8. The fungicidal composition of claim 1, wherein the fungicide (b) is Fosetil.

9. The fungicidal composition of claim 1, wherein the fungicide (b) is Fosetil and Cimoxanil.

10. The fungicidal composition of claim 1, wherein the fungicide (b) is Propamocarb, which is propyl-3-(dimethylamino)-propylcarbamate.

11. The fungicidal composition of claim 1, wherein the fungicide (b) is Chlorothalonil.

12. The fungicidal composition of claim 1, wherein the fungicide (b) is a salt of copper (I) or copper (II).

13. The fungicidal composition of claim 1, wherein the fungicide (b) is a salt of copper (I) or copper (II), and Fosetil as a mixture thereof.

14. The fungicidal composition of claim 1, wherein the fungicide (b) is a salt of copper (I) or copper (II), and Cymoxanil.

15. The fungicidal composition of claim 1, wherein the fungicide (b) is Dimethomorph.

16. The fungicidal composition of claim 1, wherein the fungicide (b) is Flumetover.

17. The fungicidal composition of claim 1, wherein the fungicide (b) is methylbenzothiadiazole-7-thiocarboxylate.

18. The fungicidal composition of claim 1, wherein the fungicide (b) is selected from the group consisting of:
1-(3-iodine-2-propinyl)-3-(3,5-dichlorophenyl)-5-methylhydantoin;
1-(3-iodine-2-propinyl)-3-(4-chlorophenyl)-5-methylhydantoin;
1-(3-iodine-2-propinyl)-3-(4-fluorophenyl)-5-methylhydantoin;
1-(3-iodine-2-propinyl)-3-(3,5-dichlorophenyl)-5,5-spiro-cyclopentanhydantoin;
1-(3-iodine-2-propinyl)-3-(3,5-dichlorophenyl)-5,5-spiro-cyclohexanhydantoin; and
1-(3-iodine-2-propinyl)-3-(3,5-dichlorophenyl)-5,5-dimethylhydantoin.

19. The fungicidal composition of claim 1, wherein the fungicide (b) is selected from the group consisting of:
N-[3'-(1'-chloro-3'-methyl-2'-oxopentane)]-3,5-dichloro-4-methylbenzamide;
N-[3'-(1'-chloro-3'-methyl-2'-oxopentane)]-3,5-dichloro-4-ethylebenzamide;
N-[3'-(1'-chloro-3'-methyl-2'-oxopentane)]-3,5-dichloro-4-ethoxybenzamide;
N-[3'-(1'-chloro-3'-methyl-2'-oxopentane)]-3,5-dichloro-4-methoxybenzamide;
N-[3'-(1'-chloro-3'-methyl-oxopentane)]-3,5-dichloro-4-cyanobenzamide; and
N-[3'-(1'-chloro-3'-methyl-2'-oxopentane)]-3,5-dibromo-4-methylbenzamide.

20. The fungicidal composition of claim 1, wherein the fungicide (b) is selected from the group consisting of:
S-R-3-[N-(N-isopropoxycarbonylvalinyl)amino]-3-isopropyl phenylpropanoate; and
S-RS-3-[N-[N-isopropoxycarbonylvalinyl)amino]-3-isopropyl phenylpropanoate.

21. The fungicidal composition of claim 1, further comprising solid carriers, liquid diluents, surface-active agents or other additives.

22. The fungicidal composition of claim 1, which further comprises other fungicides, phytoregulators, antibiotics, herbicides, insecticides, or fertilizers.

23. A method for combating fungal infections in a plant, which comprises applying an effective amount of the fungicidal composition of claim 1, to any part of a plant, seeds before planting, or to the earth where the plant grows.

24. The method of claim 23, wherein said part of said plant comprises leaves, stems, shoots branches or hypogeous parts.

25. A method for controlling phytopathogen fungi in a plant, which comprises applying an amount of the fungicidal composition of claim 1, to the seeds, leaves, roots, or the earth where the plant grows.

26. A process for preparing a compound having the formula (I), comprising:

(a) reacting a methyl ester having the formula (III):

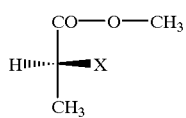

(III)

having an Z-type asymmetrical carbon and wherein X represents a halogen atom; or X represents an activated ester with an xylidine having the formula (IV):

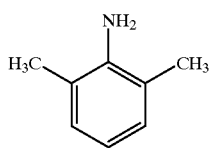

(IV)

in the presence of or without an inert organic solvent or a mixture of inert organic solvents, at a temperature ranging from 60° C. to the boiling point of the solvent system selected, in the presence of or without an organic or inorganic base, obtaining N-xylyl-D-methyl alaninate having the formula (V):

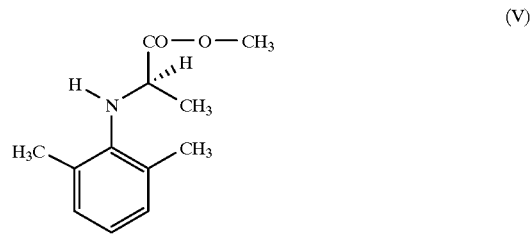

(V)

(b) acylating the N-xylyl-D-methyl alaninate having the formula (V) obtained in step (a), with a compound of phenylacetic acid; or with a mixed anhydride obtained by reaction of the salt of phenylacetic acid with an acyl chloride; or with an alkyl chloroformate; in the presence of an aromatic solvent or a halogenated solvent, or an ester solvent, at a temperature ranging from −20° C. to +40° C., in the presence of an organic or inorganic base.

27. The process of claim 26, wherein in step (b) the aromatic solvent is toluene.

28. The process of claim 26, wherein in step (b) the halogenated solvent is dichloromethane or dichlorethane.

29. The process of claim 26, wherein in step (b) the ester solvent is ethyl acetate.

30. The process of claim 26, wherein in step (b) the inorganic base is sodium bicarbonate.

31. The process of claim 26, wherein in step (b) the organic base is triethylamine or pyridine.

32. The process of claim 26, wherein in step (b) the temperature is between −5° C. and +25° C.

* * * * *